United States Patent [19]

Viti

[11] Patent Number: 4,909,438
[45] Date of Patent: Mar. 20, 1990

[54] AIR FRESHENER DISPENSER

[76] Inventor: Frank P. Viti, 707 Alton Rd., West Hempstead, N.Y. 11552

[21] Appl. No.: 213,836

[22] Filed: Jun. 30, 1988

[51] Int. Cl.⁴ .............................................. A61L 9/12
[52] U.S. Cl. ..................................... 239/34; 206/459; 239/71; 239/211
[58] Field of Search ........................... 239/34, 53–60, 239/71, 211; 40/124.1; 206/459

[56] References Cited

U.S. PATENT DOCUMENTS

| | | | |
|---|---|---|---|
| 848,434 | 3/1907 | Bradley | 239/55 |
| 978,218 | 12/1910 | Sargent | 239/54 |
| 1,589,871 | 6/1926 | Brunhoff | 239/55 |
| 2,489,707 | 11/1949 | Eubanks | 206/459 |
| 2,550,954 | 5/1951 | Benedict | 239/57 |
| 2,555,047 | 5/1951 | Logue | 239/58 |
| 2,579,715 | 12/1951 | Wilson et al. | 239/57 |
| 2,711,942 | 6/1955 | Jacquet | 239/57 |
| 2,720,419 | 10/1955 | Eby | 239/54 |
| 3,174,244 | 3/1965 | Walton | 40/124.1 |
| 3,338,395 | 8/1967 | Silverstein | 206/459 |
| 3,875,693 | 4/1975 | Pelkey | 40/124.1 |
| 4,283,011 | 2/1981 | Spector | 239/56 |
| 4,492,573 | 6/1986 | Crowell | 40/124.1 |
| 4,682,692 | 7/1987 | Kessler | 206/459 |
| 4,753,389 | 6/1988 | Davis | 239/56 |

FOREIGN PATENT DOCUMENTS 1018175 12/1952 France ........................... 40/124.1

Primary Examiner—Andres Kashnikow
Assistant Examiner—Michael J. Forman
Attorney, Agent, or Firm—Michael I. Kroll

[57] ABSTRACT

An air freshener dispenser is provided and consists of fragrance material disposed within a hollow housing having a top flat surface and a perforated side wall so that a scent can exit through the perforated side wall to permeate the ambient air thereabout and a monogram lettering kit for applying indicia onto the top flat surface of the housing to spell out a personal saying.

8 Claims, 1 Drawing Sheet

AIR FRESHENER DISPENSER

BACKGROUND OF THE INVENTION

1. Field of the Invention

The instant invention relates generally to devices for disenfecting and scenting the ambient air and more specifically it relates to an air freshener dispenser with a monogram lettering kit.

2. Description of the Prior Art

Numerous devices have been provide in prior art that are adapted to disenfect and scent the ambient air about the devices so as to make the air germ free and smell nice. While these units may be suitable for the particular purpose to which they address, they would not be as suitable for the purposes of the present invention as heretofore described.

SUMMARY OF THE INVENTION

A primary object of the present invention is to provide an air freshener dispenser that will overcome the shortcomings of the prior art devices.

Another object is to provide an air freshener dispenser that includes a monogram lettering kit which enables anyone to label the top of the housing of air freshener dispenser with anything their mind desires.

An additional object is to provide an air freshener dispenser in which the scent of fragrance material within the dispenser can match up with the material within the dispenser can match up with the shape of the housing and with the lettering applied onto the top of the housing.

A further object is to provide an air freshener dispenser that is simple and easy to use.

A still further object is to provide an air freshener dispenser that is economical in cost to manufacture.

Further objects of the invention will appear as the description proceeds.

To the accomplishment of the above and related objects, this invention may be embodied in the form illustrated in the accompanying drawings, attention being called to the fact, however, that the drawings are illustrative only, and that changes may be made in the specific construction illustrated and described within the scope of the appended claims.

BRIEF DESCRIPTION OF THE DRAWING FIGURES

DETAILED DESCRIPTION OF THE PREFERRED EMBODIMENTS

Figure 1:
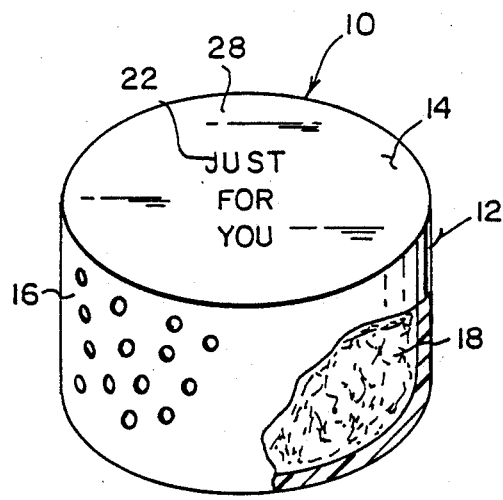
FIG. 1 is a perspective view of one form of the air freshener dispenser being cylindrical in shape with parts broken away.
Figure 2:
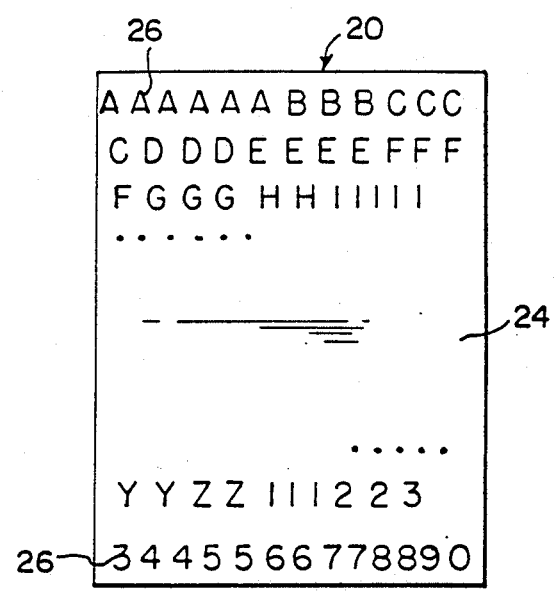
FIG. 2 is a top view of the monogram lettering kit which can be used to apply words to the top of the housing.

Turning now descriptively to the drawings, in which similar reference characters denote similar elements throughout the several views, the figures illustrate an air freshener dispenser 10 consisting of a hollow housing 12 that has a top flat surface 14 and a perforated side wall 16. Fragrance material 18 is disposed within the housing 12 so that a scent can exit through the perforated side wall 16 of the housing to permeate the ambient air thereabout. A monogram lettering kit 20 is for applying indicia 22 onto the top flat surface 14 of the housing 12.

The housing 12 is formed in any one of a number of geometric shapes and sizes and still have the top flat surface 14 and the perforated side wall 16. The monogram lettering kit 20 is at least one sheet 24 having a plurality of adhesive backed letters and numbers 26 which can be lifted off the at least one sheet 24 and placed onto the top flat surface 14 of the housing 12 to spell out a personal saying for at least one person (not shown) associated with the air freshener dispenser 10. The kit 20 can have colorful, glow in the dark, or fancy script letters and numbers 26.

The geometric shape of the housing 12, the scent of the fragrance material 18 and the personal saying applied. from the monogram lettering kit 20 onto the top flat surface 14 of the housing 12 can match up and complement each other to convey a special message therefrom. For example, the housing 12 can be in the shape of a christmas tree, the fragrance material 18 can have the scent of a pine tree while the saying can read "MERRY CHRISTMAS".

Figure 3:
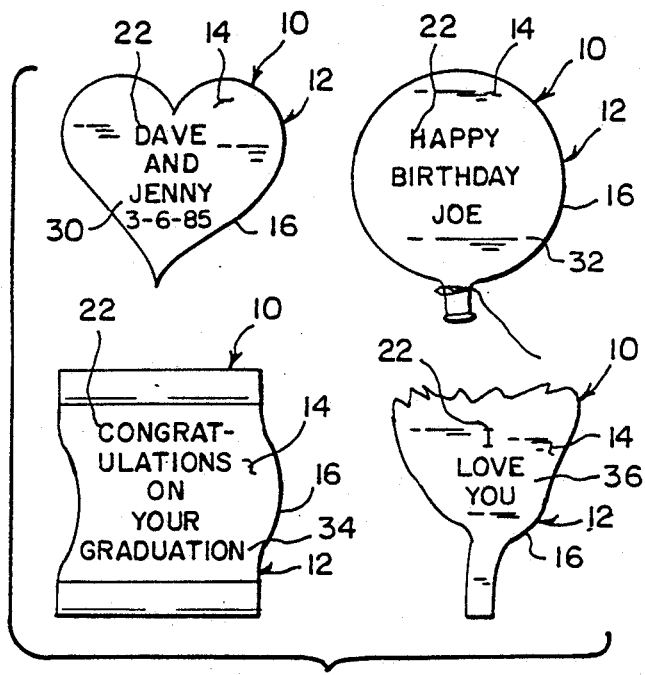
FIG. 3 is a top view of other forms of the air freshener dispenser showing various word sayings applied to the top of each of the housings thereof.

As illustrated in FIG. 1, the housing 12 is cylindrical shaped 28. In FIG. 3 the housing 12 is shown heart shaped 30, balloon shaped 32, scroll shaped 34 and flower shaped 36. Other types of shapes (not shown) can also be utilized for the configuration of the housing 12.

LIST OF REFERENCE NUMBERS

10 air freshener dispenser
12 hollow housing
14 to flat surface
16 perforated side wall
18 fragrance material
20 monogram lettering kit
22 indicia
24 sheet
26 adhesive backed letters and numbers
28 cylindrical shaped
30 heart shaped
32 balloon shaped
34 scroll shaped
36 flower shaped It will be understood that each of the elements described above, or two or more together, may also find a useful application in other types of methods differing from the type described above.

While certain novel features of this invention have been shown and described and are pointed out in the annexed claims, it is not intended to be limited to the details above, since it will be understood that various omissions, modifications, substitutions and changes in the forms and details of the device illustrated and in its operation can be made by those skilled in the art without departing in any way from the spirit of the present invention.

Without further analysis, the foregoing will so fully reveal the gist of the present invention that others can, by applying current knowledge, readily adapt it for various applications without omitting features that, from the standpoint of prior art, fairly constitute essential characteristics of the generic or specific aspects of this invention.

What is claimed is new and desired to be protected by Letters Patent is set forth in the appended claims:

1. A personalized air freshener dispenser, comprising:
   (a) a personalized hollow housing having a flat top surface and a side wall perforated with a plurality of throughbores not blindbores disposed therethrough;
   (b) a personalized fragrance material disposed within said personalized housing so that a scent can exit through said perforated side wall of said personalized housing to permeate the ambient air thereabout; and
   (c) means for applying personalized two dimensional indicia onto said flat top surface of said personalized housing, said personalized two-dimensional indicia applying means being a monogram lettering kit of at least one sheet having a plurality of adhesive backed letters and numbers which can be lifted off said at least one sheet and placed onto said personalized flat top surface of said personalized housing so that a personal saying for at least one person associated with said personalized air freshener dispenser can be spelled out.

2. A personalized air freshener dispenser as recited in claim 1, wherein said housing is formed in any one of a number of geometric shaped and sizes and still has said flat top surface and said perforated side wall.

3. A personalized air freshener dispenser as recited in claim 2, wherein said personalized hollow housing said personalized fragrance material and said personal saying applied from said monogram lettering kit onto said flat top surface of said personalized housing can complement each other to convey a special message therefrom, for example, said personalized housing can be in the shape of a Christmas tree, said personalized fragrance material can have the scent of a pine tree and the saying can read "Merry Christmas".

4. A personalized air freshener dispenser as recited in claim 3, wherein said personalized housing is cylindrically shaped.

5. A personalized air freshener dispenser as recited in claim 3, wherein said personalized housing is heart shaped.

6. A personalized air freshener dispenser as recited in claim 3, wherein said personalized housing is balloon shaped.

7. A personalized air freshener dispenser as recited in claim 3, wherein said personalized housing is scroll shaped.

8. A personalized air freshener dispenser as recited in claim 3, wherein said personalized housing is flower shaped.

* * * * *